US012616369B2

(12) United States Patent
Bolognini et al.

(10) Patent No.: US 12,616,369 B2
(45) Date of Patent: May 5, 2026

(54) COMPONENT MOUNTING SYSTEM AND METHOD FOR AN IMPLANTABLE MEDICAL DEVICE

(71) Applicant: Greatbatch Ltd., Clarence, NY (US)

(72) Inventors: Patricio Bolognini, Montevideo (UY); Luis Daniel Villamil, Montevideo (UY); Fernando Escotto, Montevideo (UY)

(73) Assignee: Greatbatch Ltd., Clarence, NY (US)

( * ) Notice: Subject to any disclaimer, the term of this patent is extended or adjusted under 35 U.S.C. 154(b) by 391 days.

(21) Appl. No.: 18/383,962

(22) Filed: Oct. 26, 2023

(65) Prior Publication Data

US 2024/0138679 A1 May 2, 2024

Related U.S. Application Data

(60) Provisional application No. 63/420,115, filed on Oct. 28, 2022.

(51) Int. Cl.
*A61B 5/00* (2006.01)
(52) U.S. Cl.
CPC ............ *A61B 5/0031* (2013.01); *A61B 5/688* (2013.01); *A61B 5/7405* (2013.01)
(58) Field of Classification Search
CPC ...... A61B 5/0031; A61B 5/688; A61B 5/7405
USPC .................................................... 340/573.1
See application file for complete search history.

(56) References Cited

U.S. PATENT DOCUMENTS

| | | | | |
|---|---|---|---|---|
| 6,137,889 A * | 10/2000 | Shennib | .............. | H04R 25/456 |
| | | | | 181/134 |
| 6,940,989 B1 * | 9/2005 | Shennib | .............. | H04R 25/606 |
| | | | | 381/328 |
| 8,473,056 B2 | 6/2013 | Engmark et al. | | |
| 2008/0064918 A1 * | 3/2008 | Jolly | .................... | A61N 1/0541 |
| | | | | 607/137 |
| 2009/0209806 A1 * | 8/2009 | Hakansson | .......... | H04R 25/606 |
| | | | | 600/25 |
| 2015/0094522 A1 * | 4/2015 | Mauger | ................ | H04R 25/606 |
| | | | | 600/25 |
| 2016/0112812 A1 * | 4/2016 | Vermeiren | .......... | H04R 25/606 |
| | | | | 600/25 |

FOREIGN PATENT DOCUMENTS

| | | |
|---|---|---|
| DE | 102008045876 | 3/2010 |
| JP | 5329925 | 10/2013 |

\* cited by examiner

*Primary Examiner* — Kerri L McNally
(74) *Attorney, Agent, or Firm* — Michael P. Horvath

(57) ABSTRACT

In various examples, an audible frequency generating system for use in an implantable device including a housing of the implantable device. The housing includes at least one wall formed to at least partially surround an interior of the housing. A frequency generator is configured to produce an audible sound within the interior of the housing. At least one conductor is electrically coupled to the frequency generator. A fastening element secures the conductor to the at least one wall of the housing, wherein the frequency generator is constrained within the housing by the at least one conductor secured to the at least one wall of the housing, such that the frequency generator includes a floating configuration relative to the housing.

20 Claims, 8 Drawing Sheets

COMPONENT MOUNTING SYSTEM AND METHOD FOR AN IMPLANTABLE MEDICAL DEVICE

CROSS REFERENCE TO RELATED APPLICATIONS

This application claims the benefit of priority to U.S. Provisional Application Ser. No. 63/420,115, filed on Oct. 28, 2022, entitled "PIEZOELECTRIC COMPONENT INSTALLED IN A FLOATING CONFIGURATION IN AN IMPLANTABLE MEDICAL DEVICE," which is incorporated by reference herein in its entirety.

BACKGROUND

A conventional configuration for producing an alarm signal in an implantable device uses a custom flex-circuit with an oscillating component that is embedded and fully adhered to an inner assembly of a device or an inner surface of an enclosure of the device. The enclosure and the inner assembly are part of the acoustic resonance. Therefore, any constraint in the device can impact sound. Additionally, the sound of the alarm signal can be affected when the function of the oscillating component is impaired by forces applied to the enclosure. For example, the sound can be impacted when the device is slightly compressed.

In another conventional configuration, an oscillating component can be fully adhered to the device assembly. Such constraint of the oscillating component does not allow the oscillating component to perform its function, and, as a result, the sound of the alarm signal produced can be affected. Considering that sound from the alarm signal can be used to notify the patient of an emergency, the reliability of this safety feature is important.

OVERVIEW

This overview is intended to provide an overview of subject matter of the present patent document. It is not intended to provide an exclusive or exhaustive explanation of the invention. The detailed description is included to provide further information about the present patent document.

The present inventors have recognized, among other things, that the present subject matter can be used to reliably mount a component within an implantable medical device. In various examples, the present subject matter is advantageous in that it decreases space requirements and, in turn, allows for a smaller device. Also, the present subject matter is advantageous in that it allows for the use of relatively inexpensive, off-the-shelf components. The present subject matter can be used to reduce, if not eliminate, the need for custom parts, potentially reducing costs and design risks associated with production of a device. The present subject matter can be used to provide a component with performance that is more immune to external forces applied on a device within which the component is mounted, thereby providing a more reliable component, such as, but not limited to, a piezoelectric alarm signal component. To better illustrate the devices described herein, a non-limiting list of examples is provided here:

Example 1 can include subject matter that can include an audible frequency generating system for use in an implantable device. The implantable device includes a power source and a control module. The audible frequency generating system includes a housing of the implantable device. The housing includes at least one wall. The at least one wall is formed to at least partially surround an interior of the housing. A frequency generator is configured to produce an audible sound, the frequency generator being disposed within the interior of the housing. At least one conductor is electrically coupled to the frequency generator. The at least one conductor operably couples the frequency generator to the power source of the implantable device to power the frequency generator and the frequency generator to the control module of the implantable device to control the frequency generator. A fastening element secures the at least one conductor to the at least one wall of the housing, wherein the frequency generator is constrained within the housing by the at least one conductor secured to the at least one wall of the housing, such that the frequency generator includes a floating configuration relative to the housing.

In Example 2, the subject matter of Example 1 is optionally configured such that the frequency generator includes a piezoelectric component.

In Example 3, the subject matter of Example 1 or Example 2 is optionally configured such that the fastening element includes at least one adhesive element.

In Example 4, the subject matter of Example 3 is optionally configured such that the adhesive element includes tape.

In Example 5, the subject matter of Example 3 or Example 4 is optionally configured such that the adhesive element includes epoxy.

In Example 6, the subject matter of any one of Examples 3-5 is optionally configured such that the adhesive element includes silicone.

In Example 7, the subject matter of any one of Examples 1-6 is optionally configured such that the fastening element includes at least one retention element, the at least one retention element being disposed within the housing of the implantable device.

In Example 8, the subject matter of Example 7 is optionally configured such that the at least one retention element includes a bracket within the housing.

In Example 9, the subject matter of Example 8 is optionally configured such that the bracket includes a constraining member coupled to the at least one wall of the housing.

In Example 10, the subject matter of Example 9 is optionally configured such that the constraining member is secured to at least one mount that is fixed to the at least one wall of the housing.

In Example 11, the subject matter of any one of Examples 1-10 is optionally configured such that the housing includes a constraining portion configured to partially constrain the frequency generator within the implantable device.

In Example 12, the subject matter of any one of Examples 1-11 is optionally configured such that the frequency generator is not directly affixed to the at least one wall of the housing, such that the frequency generator is capable of moving relative to the at least one wall of the housing.

Example 13 can include, or can optionally be combined with any one of Examples 1-12 to include subject matter that can include an audible frequency generating system for use in an implantable device. The implantable device includes a power source and a control module. The audible frequency generating system includes a housing of the implantable device including at least one wall. The at least one wall is formed to at least partially surround an interior of the housing. The housing includes a constraining portion. A frequency generator is configured to produce an audible sound. The frequency generator is disposed within the constraining portion of the housing, wherein the constraining portion is configured to allow movement of the frequency generator in a first direction but substantially limit movement of the frequency generator in at least a second direction. The second direction is different than the first direction. At least one conductor is electrically coupled to the frequency generator. The at least one conductor operably couples the frequency generator to the power source of the implantable device to power the frequency generator and the frequency generator to the control module of the implantable device to control the frequency generator. A fastening element secures the at least one conductor to the at least one wall of the housing, wherein the frequency generator is constrained within the housing by the at least one conductor secured to the at least one wall of the housing, such that the frequency generator includes a floating configuration relative to the housing.

In Example 14, the subject matter of Example 13 is optionally configured such that the fastening element includes at least one adhesive element.

In Example 15, the subject matter of Example 14 is optionally configured such that the adhesive element includes at least one of tape, epoxy, and silicone.

In Example 16, the subject matter of any one of Examples 13-15 is optionally configured such that the fastening element includes at least one retention element. The retention element is disposed within the housing of the implantable device.

In Example 17, the subject matter of Example 16 is optionally configured such that the at least one retention element includes a bracket fixed to the at least one wall of the housing.

In Example 18, the subject matter of any one of Examples 13-17 is optionally configured such that, in the floating configuration of the frequency generator, movement of the frequency generator is allowed in the first direction substantially perpendicular to the at least one wall of the housing but substantially limited in at least the second direction substantially parallel to the at least one wall of the housing.

In Example 19, the subject matter of any one of Examples 13-18 is optionally configured such that the frequency generator is not directly affixed to the at least one wall of the housing, such that the frequency generator is capable of moving relative to the at least one wall of the housing.

In Example 20, the subject matter of any one of Examples 13-19 is optionally configured such that the constraining portion includes a cavity formed within the at least one wall of the housing. The cavity is configured to partially constrain the frequency generator within the implantable device.

DETAILED DESCRIPTION

Figure 1:
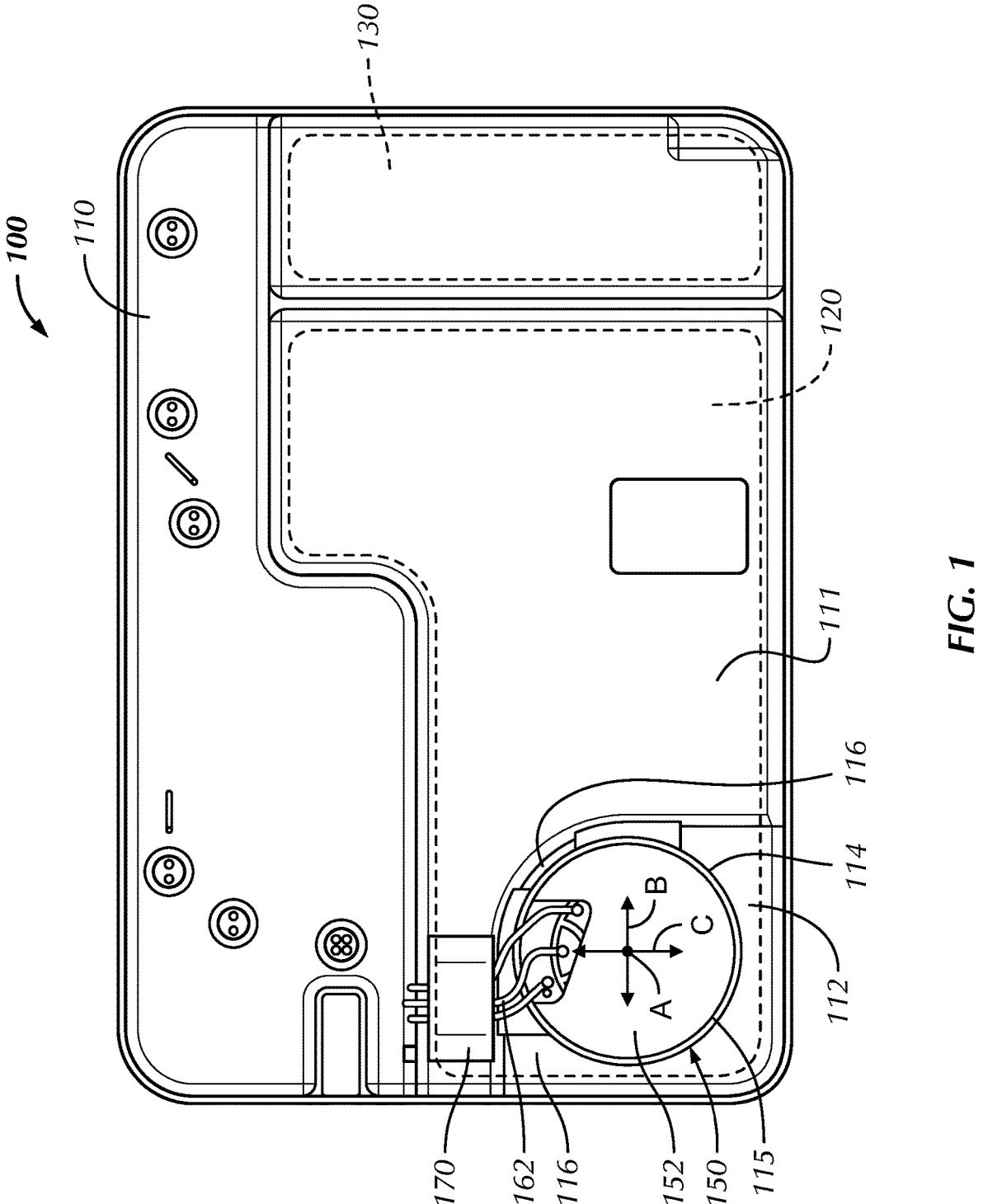
FIG. 1 is a top elevational view of a component mounted within an implantable medical device, the component mounted in accordance with at least one example of the invention.
Figure 2:
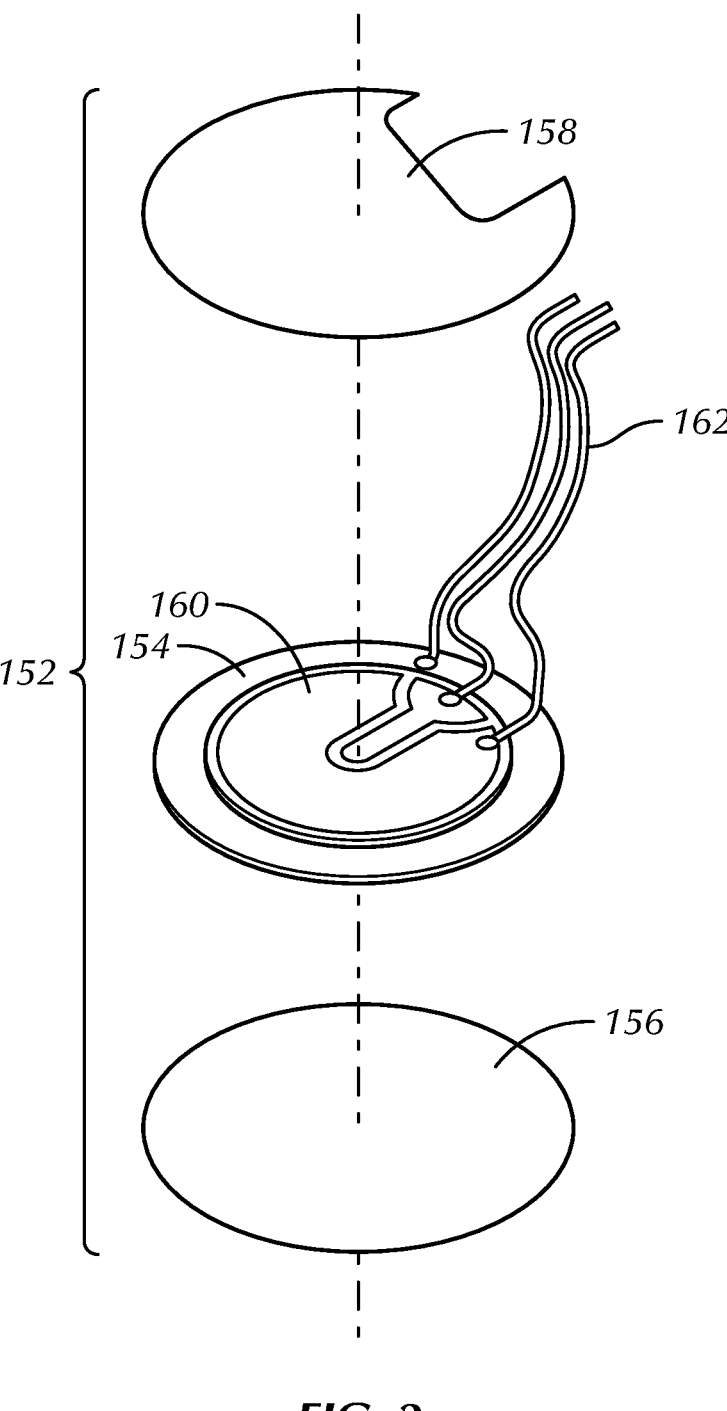
FIG. 2 is an exploded view of a component to be mounted within an implantable medical device in accordance with at least one example of the invention.

The present invention relates generally to an implantable device. More specifically, the present invention relates to mounting of a component within an implantable medical device. In some examples, the present subject matter provides for mounting of an audible frequency generator within an implantable medical device. However, the present subject matter is not intended to be so limited. As such, it is contemplated herein that the present subject matter can be to mount components other than audible frequency generators within implantable medical devices and/or mount components within devices other than implantable medical devices, such as, but not limited to, external medical devices or non-medical devices.

The present inventive subject matter, in some examples, defines an assembly configuration to mount a component, such as, for instance, a piezoelectric component configured to generate an audible alarm signal, inside an implantable device. In some examples, the present inventive subject matter is unique in that it defines a safety feature using off-the-shelf piezoelectric parts mounted in a device in such a way that shows excellent and reliable performance. In some examples, a device including the present mounting configuration for a component is not impacted by forces that may be applied to the device during the implant procedure or after being implanted. In this way, the present inventive subject matter produces a relatively reliable alarm sound at a relatively low cost, that is relatively simple to implement, and that does not require a custom solution. In some examples, the present inventive subject matter includes a relatively inexpensive and reliable solution for the implementation of an audio alarm signal for implantable devices.

In some examples, an off-the-shelf piezoelectric component can be mounted in such a way that external forces on the device do not interact with piezoelectric oscillations of the component, and, therefore, the performance of this feature is unaffected or minimally affected by the external forces acting on the device. In some examples, the present inventive subject matter allows the piezoelectric component to oscillate and/or vibrate without any constraints (such as from direct attachment of the piezoelectric component to the enclosure), thereby mounting the piezoelectric component in a floating configuration. As used herein, the term "floating configuration" is used to describe constraint of a component within a device without directly attaching the component to a portion of the device, such that the component is still able to slightly move within the device relative to the device but be constrained sufficiently to not migrate within the device to an extent to affect operation of the component itself, or any other component(s) within the device or the device itself. That is, in some examples, the component in a floating configuration will be constrained from substantial translational movement within the device without damping or otherwise hampering vibration or oscillation of the component. In this way, a frequency generator, such as, for instance, a piezoelectric component configured to generate an audible alarm signal, can be constrained within the device while still being able to produce an audible alarm signal.

In contrast, conventional systems often use custom components that are directly adhered to an inner wall of an enclosure of a device. Tape, adhesive, epoxy, or the like can be used to adhere the component to the inner wall of the enclosure. However, it has been discovered that adhesion of the component to the device enclosure limits oscillations and/or vibrations of the component, thereby degrading performance of the component. When mounting a piezoelectric component in this manner, alarm signals from the piezoelectric component become muffled, quiet, and/or inconsistent.

Since the present inventive subject matter allows the piezoelectric component to oscillate or vibrate in a floating configuration, it lessens, if not eliminates, the need for a custom development part, in some examples, but, more importantly, it allows the piezoelectric component to oscillate or vibrate without degradation of performance caused by external forces (such as those imparted by direct adhesion or other attachment of the piezoelectric component with the inner wall of the enclosure). In some examples, the present inventive subject matter includes a piezoelectric, off-the-shelf component in a floating configuration to allow the enclosure and the inner components to be part of the acoustic resonance. In this way, while the device is implanted, there are no external forces that can impact the alarm sounds, thereby increasing the reliability of this safety feature, for instance, a frequency generator configured to produce an audible alarm signal.

Referring to FIGS. 1-8, in some examples, an implantable device 100, 100', 100" can include an implantable pulse generator, including, but not limited to a cardiac pulse generator like a pacemaker or a defibrillator, a neurostimulator, or the like. In other examples, the implantable device 100, 100', 100" can include another implantable medical device, such as, but not limited to a sensing device, a physiological parameter recording device, a drug administering device, or the like. In some examples, the implantable device 100, 100', 100" includes a housing 110 surrounding internal components 120, 130 of the implantable device 100, 100', 100". For ease in portrayal of the internal aspects of the implantable device 100, 100', 100", half of the housing 110 has been removed in the figures. It should be understood that the implantable device 100, 100', 100" would include a housing 110 that completely surrounds the internal components 120, 130 and other internal aspects of the present inventive subject matter, as will be described in more detail below. In some examples, the housing 110 is formed from a material at least partially including titanium. In some examples, the housing 110 is at least partially formed from titanium and/or a titanium alloy. In other examples, the housing 110 can be formed from one or more different materials, either in addition to or in place of the titanium and/or titanium alloy, such as, but not limited to one or more of a ceramic material, a bio-compatible metallic material other than titanium or a titanium alloy, a plastic and/or polymeric material, and the like.

The internal components 120, 130 vary in type and/or number, in various examples, depending upon the type of implantable device 100, 100', 100". In some examples, a first component 120 of the internal components 120, 130 can include a control module 120, and a second component 130 of the internal components 120, 130 can include a power source 130. In some further examples, the power source 130 includes a battery. In still further examples, the power source 130 can further include a capacitor. In other examples, the first and second internal components 120, 130 can include different internal components and/or more or fewer than two internal components 120, 130, again, depending upon the type of implantable device 100, 100', 100" within which the internal components 120, 130 are disposed. For the sake of simplicity, the remainder of the description will refer to the first and second internal components 120, 130 as the control module 120 and the power source 130, respectively. However, it is to be understood that the present inventive subject matter is not so limited.

In some examples, the implantable device 100, 100', 100" includes an audible frequency generating system 150, 150', 150" configured to selectively produce an audible sound. In some examples, the audible frequency generating system 150, 150', 150" is configured to produce an alarm that is capable of being heard by a patient within whom the implantable device 100, 100', 100" is implanted or another person, such as, for instance, a physician or other caregiver, in close proximity to the patient. Such an alarm can be useful to inform the patient, physician, and/or caregiver of an issue with the implantable device 100, 100', 100", such as, but not limited to, one or more of a low-charge condition, an error condition, a physiological event (such as, but not limited to, an arrhythmia or other cardiac event, elevated pressure, low blood sugar, etc.), a device event (such as, but not limited to, an administered stimulation pulse, an administered drug dosage, a communication sent from or received by the implantable device 100, 100', 100", etc.), the inability to establish communication between the implantable device 100, 100', 100" and an external device, and a hardware or software malfunction, to name a few.

In some examples, the audible frequency generating system 150, 150', 150" for use in the implantable device 100, 100', 100" is disposed within the housing 110 of the implantable device 100, 100', 100". In some examples, the implantable device 100, 100', 100" includes the power source 130 and the control module 120 also disposed within the housing 110. In some examples, the implantable device 100, 100', 100" includes additional and/or alternative internal components; however, for the sake of simplicity, any such additional and/or alternative components have been omitted from the figures in order to clearly portray the inventive aspects of the present subject matter. In some examples, the housing 110 of the implantable device 100, 100', 100" includes at least one wall 112, with the at least one wall 112 being formed to at least partially surround an interior 111 of the housing 110. As described above, only part of the housing 110 is shown in the figures for ease of portrayal of the internal aspects of the present inventive subject matter. In actuality, in some examples, the housing 110 surrounds and hermetically seals the interior 111 of the housing 110 to allow for implantation of the implantable device 100, 100', 100" within a patient.

In some examples, the audible frequency generating system 150, 150', 150" includes a frequency generator 152 configured to produce an audible sound, the frequency generator 152 being disposed within the interior 111 of the housing 110. In some examples, the frequency generator 152 includes a sound-generating component 160 configured to produce an audible-frequency sound. In some examples, the sound-generating component 160 is disposed on a substrate 154. The substrate 154, in some examples, can include a metal plate, although this is not intended to be limiting as the substrate 154 can be formed from any suitable material. The sound-generating component 160, in some examples, can be a piezoelectric component 160. In some examples, the sound-generating component 160 includes a buzzer 160. The sound-generating component 160, in some examples, is relatively thin and disc-like. Since space is typically at a premium within implantable devices, in some examples, the sound-generating component 160 is relatively small so as to not take up too much space within the implantable device 100, 100', 100". In some examples, the frequency generator 152 includes a first insulation film 156 on one side of the sound-generating component 160 and a second insulation film 158 on the other side of the sound-generating component 160 in order to electrically insulate the sound-generating component 160 from the housing 110 and/or any components or features of the implantable device 100, 100', 100" to which the sound-generating component 160 is not supposed to be electrically coupled. In some examples, the first and/or second insulation films 156, 158 are/is used to guard against electrical contact between the housing 110 and the sound-generating component 160.

In some examples, the frequency generator 152 includes at least one conductor 162 electrically coupled to the frequency generator 152. In some examples, the frequency generator 152 includes three conductors 162 electrically coupled to the frequency generator 152; however, this is not intended to be limiting. For instance, in other examples, the frequency generator 152 can include more or fewer than three conductors 162, provided the proper electrical connections are made to allow the frequency generator 152 to function within the implantable device 100, 100', 100". In some examples, the at least one conductor 162 operably couples the frequency generator 152 to the power source 130 of the implantable device 100, 100', 100" to power the frequency generator 152. In some examples, the at least one conductor 162 operably couples the frequency generator 152 to the control module 120 of the implantable device 100, 100', 100" to control the frequency generator 152. In other examples, the at least one conductor 162 electrically couples the frequency generator 152 to other components and/or aspects of the implantable device 100, 100', 100" depending upon the usage of the frequency generator 152 and how the audible sound of the frequency generator 152 is intended to be used to alert the patient, physician, or other caregiver.

In some examples, a fastening element 170, 170', 170" secures the at least one conductor 162 to the at least one wall 112 of the housing 110 to constrain the frequency generator 152 within the housing 110 by the at least one conductor 162 secured to the at least one wall 112 of the housing 110. In this way, in some examples, the frequency generator 152 is constrained in a floating configuration relative to the housing 110. That is, in some examples, the sound-generating component 160 is allowed to move at least slightly relative to the housing 110 to allow for the frequency generator 152 to produce the audible sound without the audible sound being overly muted or distorted. As described above, such a muted or distorted sound is often produced if a frequency generator is adhered or otherwise attached directly to the wall of the housing, as is common in typical implanted devices. The present inventive subject matter, in some examples, seeks to remedy this issue of muted or distorted sound by providing the audible frequency generating system 150, 150', 150" with the floating configuration in which the frequency generator 152 (more specifically, the sound-generating component 160 of the frequency generator 152) is not directly adhered, directly affixed, or otherwise directly attached to the at least one wall 112 of the housing 110. In some examples, the frequency generator 152 in the floating configuration is able to vibrate relative to the at least one wall 112 of the housing 110 to produce the audible sound. In some examples, by securing the at least one conductor 162 to the at least one wall 112 of the housing 110, the fastening element 170, 170', 170" constrains the frequency generator 152 within the housing 110 to inhibit the frequency generator 152 from migrating within the interior 111 of the housing 110, thereby reducing the possibility of the frequency generator 152 moving within the implantable device 100, 100', 100" and potentially shorting out or otherwise damaging an internal component or other aspect of the implantable device 100, 100', 100" or damaging the frequency generator 152 itself. It is noted that, in some examples, by constraining the at least one conductor 162 with the fastening element 170, 170', 170" and not directly affixing the frequency generator 152 (or, more specifically, the sound-generating component 160, the substrate 154, the first insulation film 156, and/or the second insulation film 158) to the at least one wall 112 of the housing 110, flexibility of the at least one conductor 162 allows for at least some play in the sound-generating component 160 with respect to the at least one wall 112 of the housing 110 to allow for vibration and, in turn, sound generation, of the sound-generating component 160.

Figure 3:
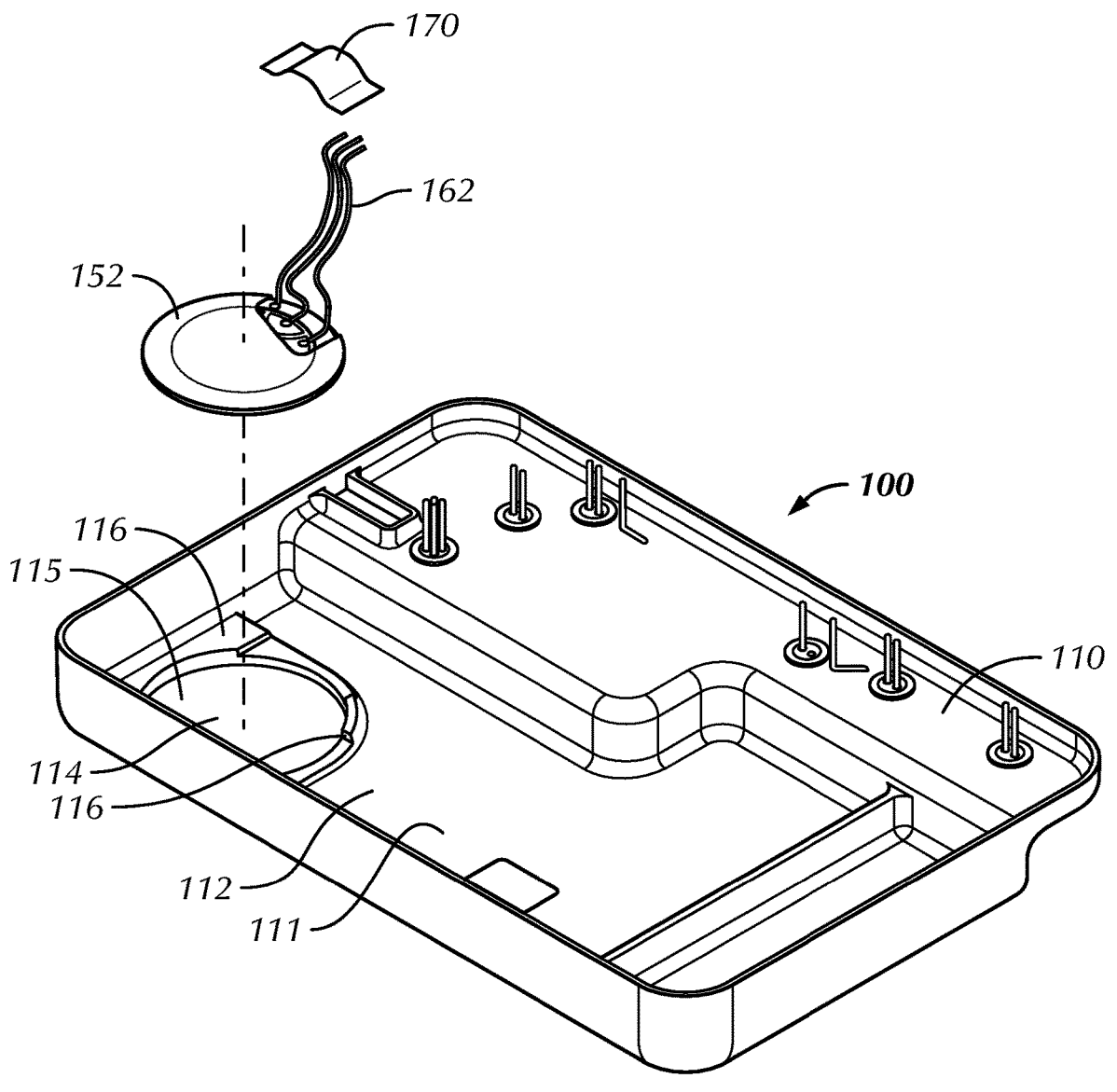
FIG. 3 is an exploded view of the component mounted within the implantable medical device, the component mounted in accordance with at least the example of FIG. 1.
Figure 4:
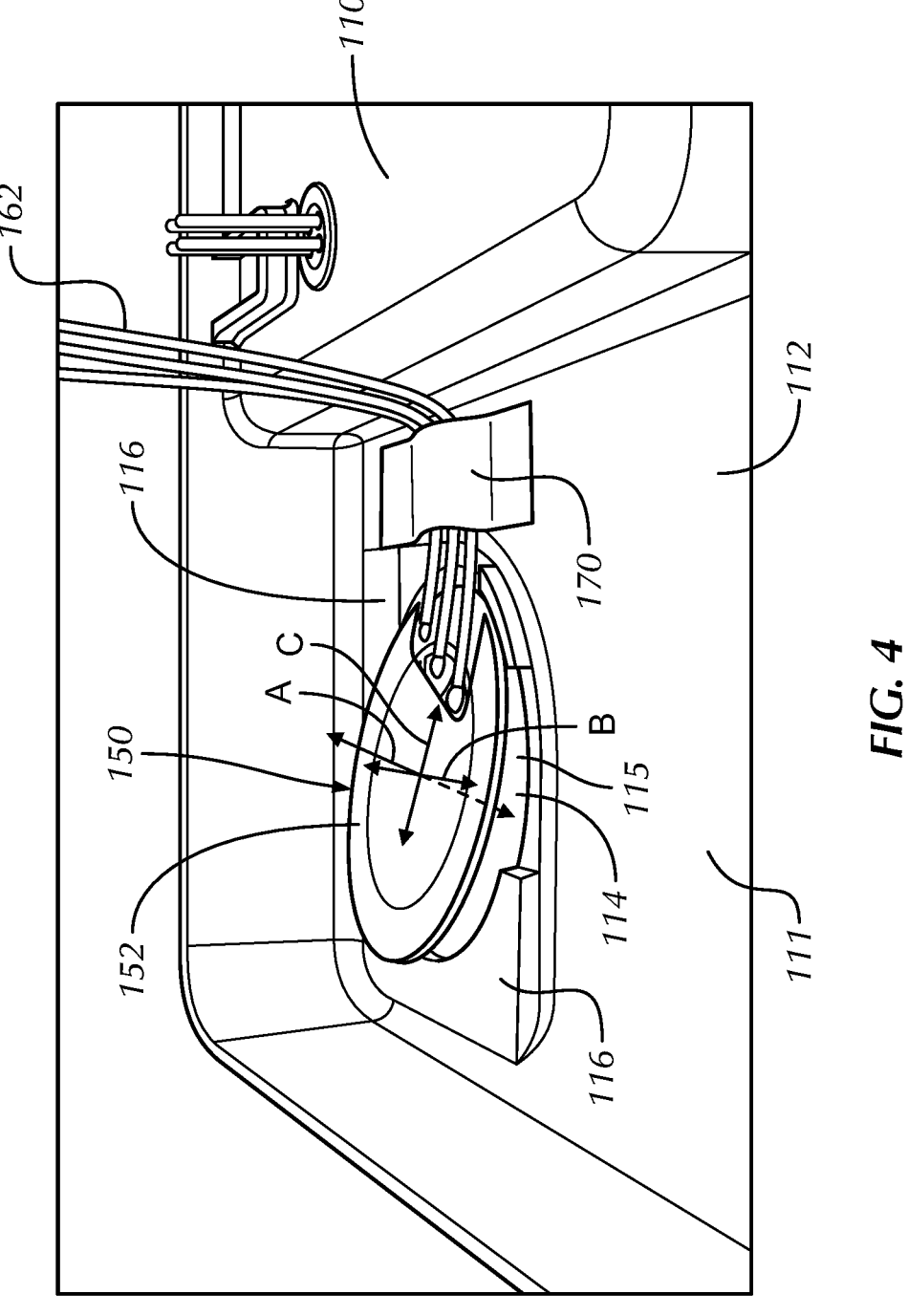
FIG. 4 is a side perspective view of the component mounted within the implantable medical device, the component mounted in accordance with at least the example of FIG. 1.

Referring to FIGS. 1 and 3-6, in some examples, the fastening element 170, 170' includes at least one adhesive element 170, 170'. Referring specifically to FIGS. 1, 3, and 4, in some examples, the adhesive element 170 includes tape 170. The tape 170, in some examples, is affixed to the at least one wall 112 of the housing 110 and disposed across the at least one conductor 162 to capture the at least one conductor 162 between the tape 170 and the at least one wall 112 of the housing 110. In this way, in some examples, the tape 170 acts to constrain the at least one conductor 162 with respect to the housing 110 in order to indirectly constrain the frequency generator 152 (and more specifically, the sound-generating component 160) within the interior 111 of the housing 110, such that the frequency generator 152 is disposed in the floating configuration within the interior 111 of the housing 110.

Figure 5:
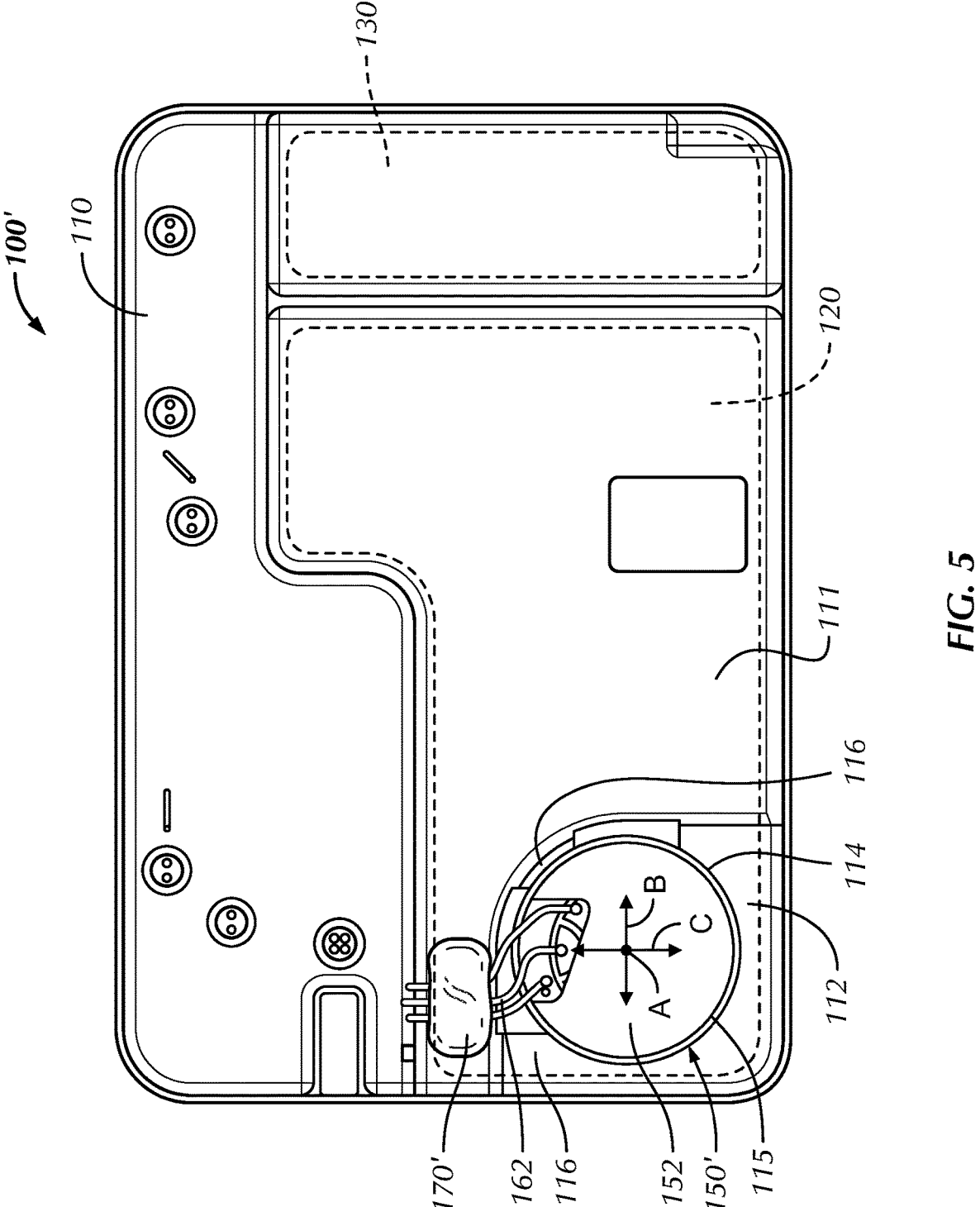
FIG. 5 is a top elevational view of a component mounted within an implantable medical device, the component mounted in accordance with at least one example of the invention.
Figure 6:
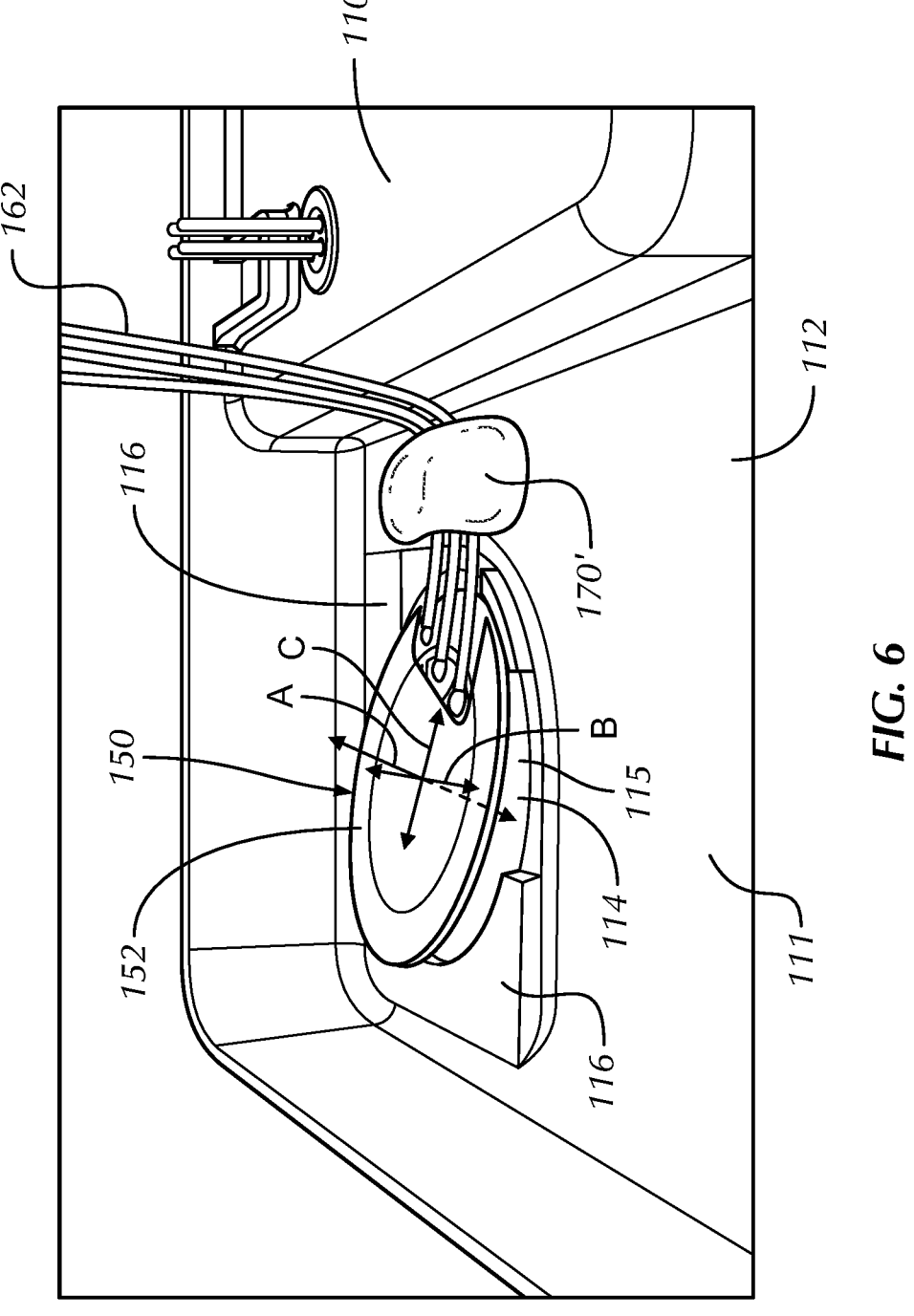
FIG. 6 is a side perspective view of the component mounted within the implantable medical device, the component mounted in accordance with at least the example of FIG. 5.

Now referring specifically to FIGS. 5 and 6, in some examples, the adhesive element 170' includes an adhesive resin or glue 170', such as, but not limited to, one or more of epoxy, silicone, urethane, or the like. The adhesive resin, putty, or glue 170', in some examples, is affixed to the at least one wall 112 of the housing 110 and disposed across the at least one conductor 162 to capture the at least one conductor 162 between the adhesive resin, putty, or glue 170' and the at least one wall 112 of the housing 110. In some examples, the adhesive resin, putty, or glue 170' is dispensed across the one or more conductors 162 and allowed to cure to affix the one or more conductors 162 to the at least one wall 112 of the housing 110. In this way, in some examples, the adhesive resin, putty, or glue 170' acts to constrain the at least one conductor 162 with respect to the housing 110 in order to indirectly constrain the frequency generator 152 (and more specifically, the sound-generating component 160) within the interior 111 of the housing 110, such that the frequency generator 152 is disposed in the floating configuration within the interior 111 of the housing 110.

Figure 7:
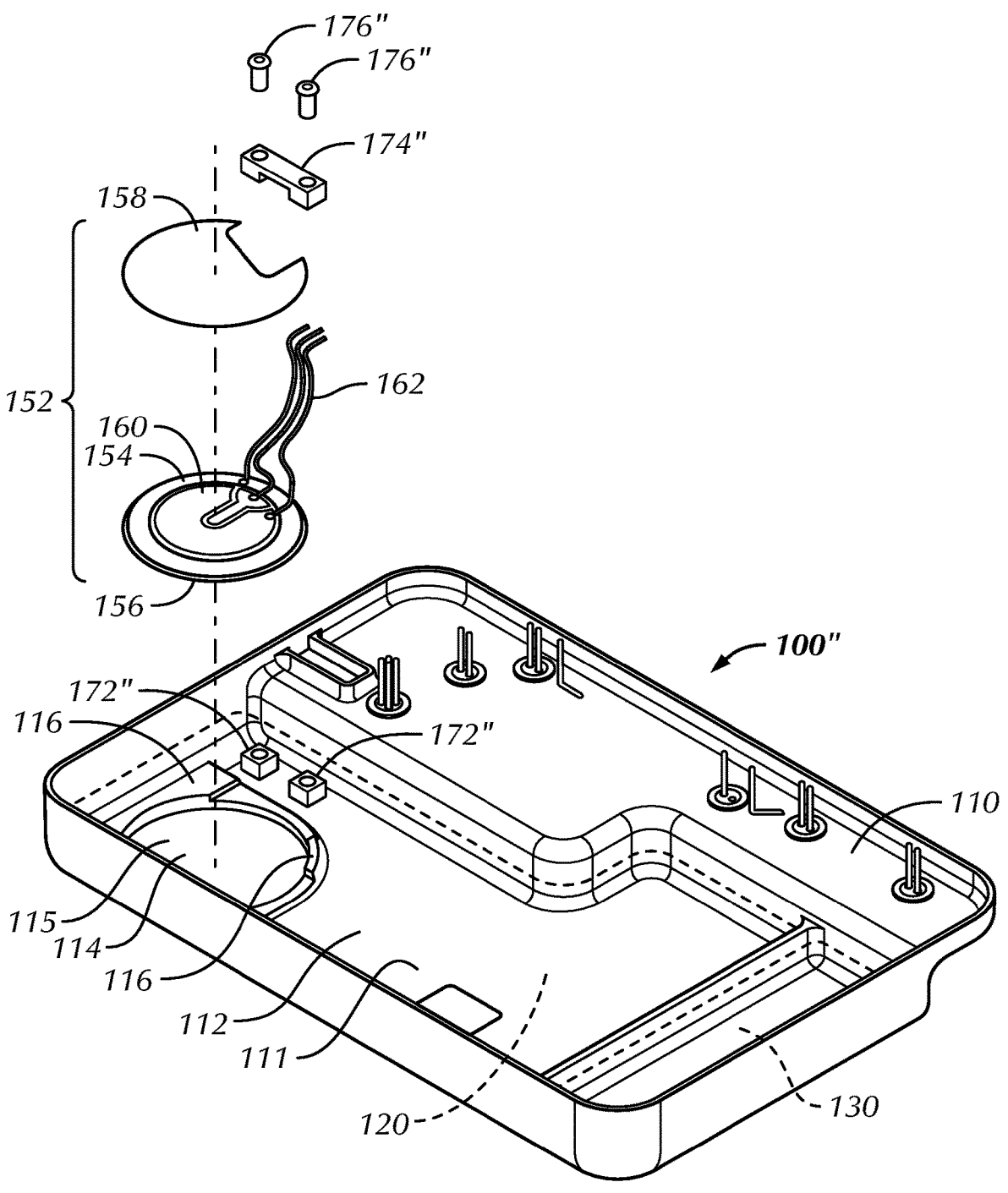
FIG. 7 is an exploded view of a component mounted within an implantable medical device, the component mounted in accordance with at least one example of the invention.
Figure 8:
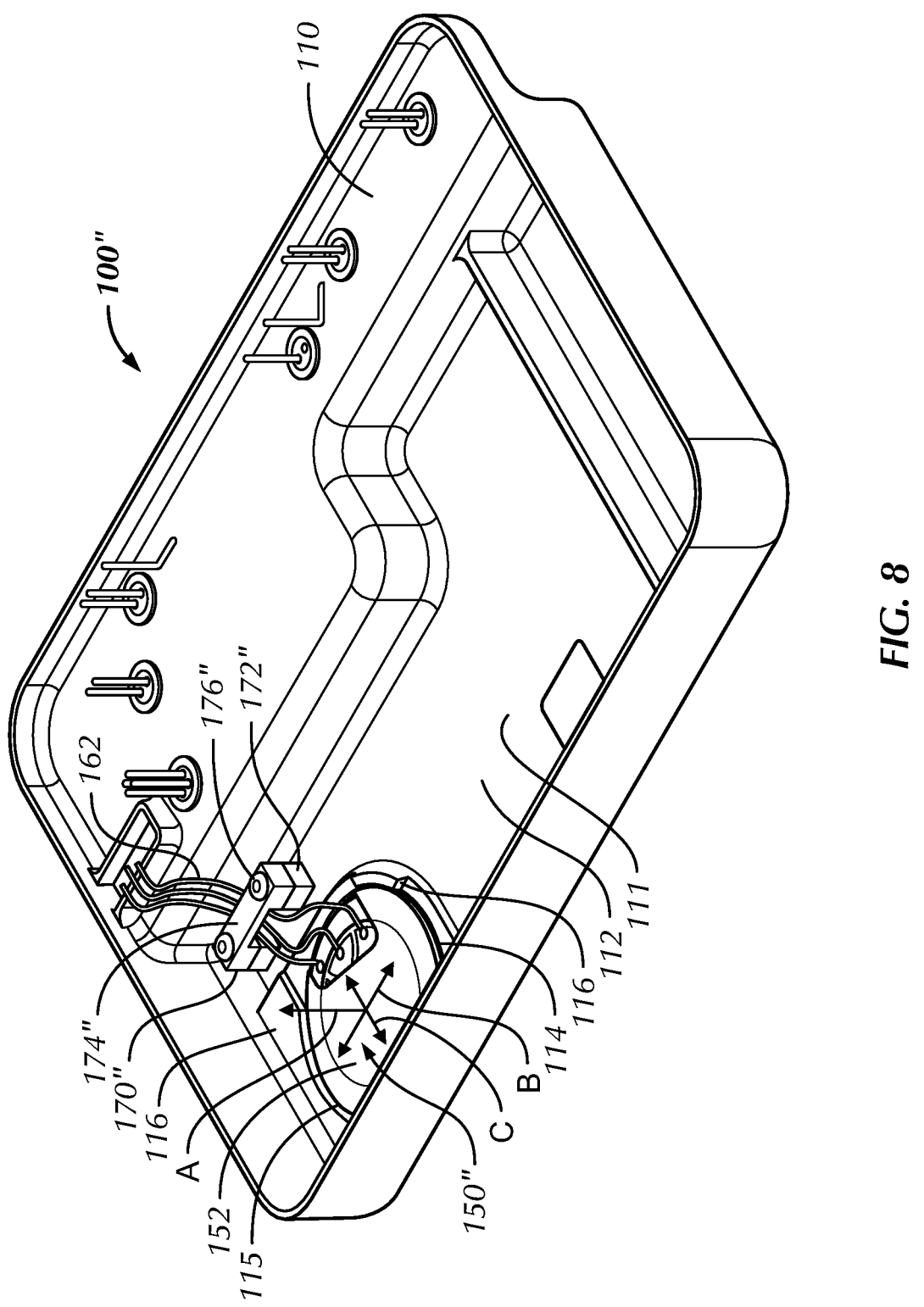
FIG. 8 is a perspective view of the component mounted within the implantable medical device, the component mounted in accordance with at least the example of FIG. 7.

Referring now to FIGS. 7 and 8, in some examples, the fastening element 170" includes at least one retention element 170", the at least one retention element 170" being disposed within the housing 110 of the implantable device 100. In some examples, the at least one retention element 170" includes a bracket 170" within the housing 110. In some examples, the bracket 170" is mounted or otherwise fixed to the at least one wall 112 of the housing 110. The bracket 170", in some examples, includes a constraining member 174" coupled to the at least one wall 112 of the housing 110. In some examples, the constraining member 174" includes a bar or other member sized and shaped to inhibit the at least one conductor 162 from moving excessively when constrained by the constraining member 174". In some examples, the constraining member 174" is secured to at least one mount 172" that is fixed to the at least one wall 112 of the housing 110. In some examples, the constraining member 174" spans across two mounts 172" that are fixed to the at least one wall 112 of the housing 110. In some examples, the at least one mount 172" is separately formed from the housing 110 and is affixed to the at least one wall 112 of the housing 110 using welding, soldering, brazing, adhesives, or the like. In other examples, the at least one mount 172" is integrally formed with the housing 110, such that the at least one mount 172" extends outwardly from the at least one wall 112 of the housing 110. In some examples, one or more fasteners 176" are used to attach the constraining member 174" to the at least one mount 172". In other examples, the constraining member 174" is attached to the at least one mount 172" using welding, soldering, brazing, adhesives, or the like. The bracket 170", in some examples, is affixed to the at least one wall 112 of the housing 110 and disposed across the at least one conductor 162 to capture the at least one conductor 162 between the bracket 170" and the at least one wall 112 of the housing 110. In this way, in some examples, the bracket 170" acts to constrain the at least one conductor 162 with respect to the housing 110 in order to indirectly constrain the frequency generator 152 (and more specifically, the sound-generating component 160) within the interior 111 of the housing 110, such that the frequency generator 152 is disposed in the floating configuration within the interior 111 of the housing 110.

In some examples, a combination of the tape 170, the adhesive resin or glue 170', and/or retention element 170" can be used to constrain the at least one conductor 162 with respect to the housing 110. In some examples, multiple retention elements 170" can be formed with or attached to the housing 110 to constrain the one or more conductors 162 within the housing 110. In this way, in some examples, the sound-generating component 160 itself is not adhered, glued, or otherwise firmly attached to the housing 110 and is, instead, "floating" with respect to the housing 110 in the floating configuration. In this way, the sound-generating component 160 is maintained in position within the housing 110 by constraining the one or more conductors 162 using one or more of the tape 170, the adhesive resin or glue 170', and/or retention element 170", or a combination thereof, thereby allowing the sound-generating component 160 to oscillate and/or vibrate relatively freely with little to no constraint.

Referring now to FIGS. 1 and 3-8, in some examples, the housing 110 of the implantable device 100, 100', 100" includes a constraining portion 114 configured to partially constrain the frequency generator 152 within the implantable device 100, 100', 100". In some examples, the housing 110 includes the at least one wall 112 formed to at least partially surround the interior 111 of the housing 110 and including the constraining portion 114 formed within an interior surface of the at least one wall 112 of the housing 110. In some examples, the frequency generator 152 is disposed within the constraining portion 114 of the housing 110. The constraining portion 114, in some examples, is configured to allow movement of the frequency generator 152 in a first direction A but substantially limit movement of the frequency generator 152 in at least a second direction B, the second direction B being different than the first direction A. In some examples, the constraining portion 114 is further configured to allow movement of the frequency generator 152 in the first direction A but substantially limit movement of the frequency generator 152 in the second direction B and a third direction C, the third direction C being different than the first direction A and the second direction B. In some examples, the constraining portion 114 at least partially constrains the frequency generator 152 in directions substantially parallel to the at least one wall 112 of the housing 110 but allows at least limited movement of the frequency generator 152 in a direction substantially perpendicular to the at least one wall 112 of the housing 110. In some examples, the constraining portion 114 includes a cavity 115 formed within the at least one wall 112 of the housing 110, the cavity 115 being configured to partially constrain the frequency generator 152 within the implantable device 100, 100', 100". In some examples, the constraining portion 114 includes one or more cavity walls or other barrier structures 116 around the cavity 115 extending outwardly from the at least one wall 112 of the housing 110 to better build up and define the cavity 115 in order to accept the frequency generator 152 within the cavity 115 of the constraining portion 114. In some examples, a geometry of the constraining portion 114 amplifies the sound generated by the sound-generating component 160. In some examples, the constraining portion 114 of the at least one wall 112 of the housing 110 aids placement of the sound-generating component 160 during the installation of the sound-generating component 160 within the implantable device 100, 100', 100". In other examples, the constraining portion 114 can be eliminated from the at least one wall 112 of the housing 110, such that the frequency generator 152 is disposed on a relatively flat portion of the at least one wall 112 of the housing 110. In some examples, the cavity 115 can be integrally formed within the at least one wall 112 of the housing 110. In other examples, the cavity 115 can be formed by the one or more cavity walls 116 at least partially surrounding the cavity 115. In still other examples, the cavity 115 can be integrally formed within the at least one wall 112 of the housing 110 and additionally formed by the one or more cavity walls 116 at least partially surrounding the cavity 115. In some examples, the cavity walls 116 are integrally formed with the at least one wall 112 of the housing 110. In other examples, the cavity walls 116 are affixed to the at least one wall 112 of the housing 110 using a joining technique, such as, but not limited to, welding, soldering, brazing, adhesives, or the like. In this way, in some examples, with the fastening element 170, 170', 170" securing the at least one conductor 162 to the at least one wall 112 of the housing 110, the frequency generator is constrained within the housing by the at least one conductor 162 secured to the at least one wall 112 of the housing 110 as well as by the constraining portion 114, such that the frequency generator 152 "floats" in the floating configuration relative to the housing 110, wherein at least slight movement of the frequency generator 152 (and, more specifically, the sound-generating component 160) is permitted in the first direction A (substantially perpendicular to the at least one wall 112 of the housing 110) but movement of the frequency generator 152 (and, more specifically, the sound-generating component 160) is substantially inhibited in the second direction B and/or the third direction C (substantially parallel to the at least one wall 112 of the housing 110).

In some examples, a length of the at least one conductor 162 (measured between the fastening elements 170, 170', 170" and a connection point to the frequency generator 152) is sufficient to allow for at least some movement of the frequency generator 152 in the first direction A but not too long so as to allow for excessive migration of the frequency generator 152 within the interior 112 of the housing 110. For instance, in some examples, the length of the at least one conductor 162 is between about 8 mm and about 12 mm. In some examples, the length of the at least one conductor 162 is between 9 mm and 11 mm. In other examples, the length of the at least one conductor 162 is between 9.5 mm and 10.5 mm. The length of the at least one conductor 162, in some examples, is about 10 mm.

In some examples, a diameter of the frequency generator 152 is smaller than a diameter of the cavity 115 of the constraining portion 114 to allow for movement of the frequency generator 152 in the first direction A (that is, there is no frictional restraint of the frequency generator 152 by the cavity 115 or the walls 116) but substantially inhibit movement of the frequency generator 152 in the second direction B and/or the third direction C. In some examples, the diameter of the frequency generator 152 is between about 19 mm and about 21 mm, and the diameter of the cavity 115 is between about 21 mm and about 23 mm. In other examples, the diameter of the frequency generator 152 is between 19.9 mm and 20.1 mm, and the diameter of the cavity 115 of the constraining portion 114 is between 21.9 mm and 22.1 mm. In some examples, the diameter of the frequency generator 152 is about 20 mm, and the diameter of the cavity 115 is about 22 mm. In still other examples, the diameter of the frequency generator 152 is about 2 mm larger than the diameter of the cavity 115.

In use, with reference to the description above and FIGS. 1-8, in some examples, the present inventive subject matter provides a method of mounting a component, such as, but not limited to, the sound-generating component 160 of the audible frequency generating system 150, 150', 150", within the implantable device 100, 100', 100". As described in more detail above, in some examples, the method includes placing the frequency generator 152 within the housing 110 of the implantable device 100, 100', 100". The method further includes, in some examples, indirectly constraining the frequency generator 152 using one or more of the fastening elements 170, 170', 170" to secure the at least one conductor 162 to the at least one wall 112 of the housing 110. In some examples, the method includes placing the frequency generator 152 within the constraining portion 114 to at least partially constrain the frequency generator 152 within the housing 110 of the implantable device 100, 100', 100", either instead of or in addition to indirectly constraining the frequency generator 152 using one or more of the fastening elements 170, 170', 170". In this way, in some examples, the frequency generator 152 "floats" in the floating configuration relative to the housing 110, the frequency generator 152 is constrained within the housing 110 by the at least one conductor 162 secured to the at least one wall 112 of the housing 110 and/or by the frequency generator 152 being disposed within the constraining portion 114, such that at least slight movement of the frequency generator 152 is allowed (and, more specifically, the sound-generating component 160) in the first direction A (substantially perpendicular to the at least one wall 112 of the housing 110) and movement of the frequency generator 152 (and, more specifically, the sound-generating component 160) is substantially inhibited in the second direction B and/or the third direction C (substantially parallel to the at least one wall 112 of the housing 110).

The present inventors have recognized various advantages of the subject matter described herein. The present inventors have recognized, among other things, that the present subject matter can be used to reliably mount a component within an implantable medical device. In various examples, the present subject matter is advantageous in that it decreases space requirements and, in turn, allows for a smaller device. Also, the present subject matter is advantageous in that it allows for the use of relatively inexpensive, off-the-shelf components. The present subject matter can be used to reduce, if not eliminate, the need for custom parts, potentially reducing costs and design risks associated with production of a device. The present subject matter can be used to provide a component with performance that is more immune to external forces applied on a device within which the component is mounted, thereby providing a more reliable component, such as, but not limited to, a piezoelectric alarm signal component. While various advantages of the example systems are listed herein, this list is not considered to be complete, as further advantages may become apparent from the description and figures presented herein.

Although the subject matter of the present patent application has been described with reference to various examples, workers skilled in the art will recognize that changes can be made in form and detail without departing from the scope of the subject matter recited in the below claims.

The above Detailed Description includes references to the accompanying drawings, which form a part of the Detailed Description. The drawings show, by way of illustration, specific examples in which the present apparatuses and methods can be practiced. These embodiments are also referred to herein as "examples."

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled. In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "about" and "approximately" or similar are used to refer to an amount that is nearly, almost, or in the vicinity of being equal to a stated amount.

In the appended claims, the terms "including" and "in which" are used as the plain-English equivalents of the respective terms "comprising" and "wherein." Also, in the following claims, the terms "including" and "comprising" are open-ended, that is, an apparatus or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

The invention claimed is:

1. An audible frequency generating system for use in an implantable device, the implantable device including a power source and a control module, the audible frequency generating system comprising:
   a housing of the implantable device, the housing including at least one wall, the at least one wall being formed to at least partially surround an interior of the housing;
   a frequency generator configured to produce an audible sound, the frequency generator being disposed within the interior of the housing;
   at least one conductor electrically coupled to the frequency generator, the at least one conductor operably coupling:
      the frequency generator to the power source of the implantable device to power the frequency generator; and
      the frequency generator to the control module of the implantable device to control the frequency generator; and
   a fastening element securing the at least one conductor to the at least one wall of the housing, wherein the frequency generator is constrained within the housing by the at least one conductor secured to the at least one wall of the housing, such that the frequency generator includes a floating configuration relative to the housing.

2. The audible frequency generating system of claim 1, wherein the frequency generator includes a piezoelectric component.

3. The audible frequency generating system of claim 1, wherein the fastening element includes at least one adhesive element.

4. The audible frequency generating system of claim 3, wherein the adhesive element includes tape.

5. The audible frequency generating system of claim 3, wherein the adhesive element includes epoxy.

6. The audible frequency generating system of claim 3, wherein the adhesive element includes silicone.

7. The audible frequency generating system of claim 1, wherein the fastening element includes at least one retention element, the at least one retention element being disposed within the housing of the implantable device.

8. The audible frequency generating system of claim 7, wherein the at least one retention element includes a bracket within the housing.

9. The audible frequency generating system of claim 8, wherein the bracket includes a constraining member coupled to the at least one wall of the housing.

10. The audible frequency generating system of claim 9, wherein the constraining member is secured to at least one mount that is fixed to the at least one wall of the housing.

11. The audible frequency generating system of claim 1, wherein the housing includes a constraining portion configured to partially constrain the frequency generator within the implantable device.

12. The audible frequency generating system of claim 1, wherein the frequency generator is not directly affixed to the at least one wall of the housing, such that the frequency generator is capable of moving relative to the at least one wall of the housing.

13. An audible frequency generating system for use in an implantable device, the implantable device including a power source and a control module, the audible frequency generating system comprising:
   a housing of the implantable device including at least one wall, the at least one wall being formed to at least partially surround an interior of the housing, the housing including a constraining portion;
   a frequency generator configured to produce an audible sound, the frequency generator being disposed within the constraining portion of the housing, wherein the constraining portion is configured to allow movement of the frequency generator in a first direction but substantially limit movement of the frequency generator in at least a second direction, the second direction being different than the first direction;
   at least one conductor electrically coupled to the frequency generator, the at least one conductor operably coupling:
      the frequency generator to the power source of the implantable device to power the frequency generator; and
      the frequency generator to the control module of the implantable device to control the frequency generator; and
   a fastening element securing the at least one conductor to the at least one wall of the housing, wherein the frequency generator is constrained within the housing by the at least one conductor secured to the at least one wall of the housing, such that the frequency generator includes a floating configuration relative to the housing.

14. The audible frequency generating system of claim 13, wherein the fastening element includes at least one adhesive element.

15. The audible frequency generating system of claim 14, wherein the adhesive element includes at least one of tape, epoxy, and silicone.

16. The audible frequency generating system of claim 13, wherein the fastening element includes at least one retention element, the retention element being disposed within the housing of the implantable device.

17. The audible frequency generating system of claim 16, wherein the at least one retention element includes a bracket fixed to the at least one wall of the housing.

18. The audible frequency generating system of claim 13, wherein, in the floating configuration of the frequency generator, movement of the frequency generator is allowed in the first direction substantially perpendicular to the at least one wall of the housing but substantially limited in at least the second direction substantially parallel to the at least one wall of the housing.

19. The audible frequency generating system of claim 13, wherein the frequency generator is not directly affixed to the at least one wall of the housing, such that the frequency generator is capable of moving relative to the at least one wall of the housing.

20. The audible frequency generating system of claim 13, wherein the constraining portion includes a cavity formed within the at least one wall of the housing, the cavity being configured to partially constrain the frequency generator within the implantable device.

* * * * *